United States Patent
Floto et al.

(10) Patent No.: US 11,926,813 B2
(45) Date of Patent: Mar. 12, 2024

(54) CELL COLONY PICKING SYSTEM

(71) Applicant: Molecular Devices, LLC, San Jose, CA (US)

(72) Inventors: Timothy A. Floto, Scotts Valley, CA (US); Alison A. Glaser, Philadelphia, PA (US); Lee Von Landau, Hampshire (GB); John Phillips, San Jose, CA (US); Kyle Corey, San Jose, CA (US); Padmavathi Bandhuvula, Fremont, CA (US); Anna Louise Forsyth, Sunnyvale, CA (US)

(73) Assignee: Molecular Devices, LLC, San Jose, CA (US)

( * ) Notice: Subject to any disclaimer, the term of this patent is extended or adjusted under 35 U.S.C. 154(b) by 496 days.

(21) Appl. No.: 16/618,714

(22) PCT Filed: Jun. 4, 2018

(86) PCT No.: PCT/US2018/035901
§ 371 (c)(1),
(2) Date: Dec. 2, 2019

(87) PCT Pub. No.: WO2018/223142
PCT Pub. Date: Dec. 6, 2018

(65) Prior Publication Data
US 2020/0131465 A1  Apr. 30, 2020

Related U.S. Application Data

(60) Provisional application No. 62/514,747, filed on Jun. 2, 2017.

(51) Int. Cl.
*C12M 1/34* (2006.01)
*C12M 1/36* (2006.01)
(Continued)

(52) U.S. Cl.
CPC ............ *C12M 41/36* (2013.01); *C12M 41/48* (2013.01); *G01N 21/17* (2013.01);
(Continued)

(58) Field of Classification Search
None
See application file for complete search history.

(56) References Cited

U.S. PATENT DOCUMENTS

| | | |
|---|---|---|
| 2013/0217061 A1 | 8/2013 | Sato et al. |
| 2014/0232844 A1 | 8/2014 | Wolff et al. |
| 2017/0108686 A1 | 4/2017 | Chan et al. |

FOREIGN PATENT DOCUMENTS

| | | |
|---|---|---|
| JP | 2014-502146 A | 1/2014 |
| WO | 2016193200 A1 | 12/2016 |

OTHER PUBLICATIONS

International Search Report and Written Opinion for PCT/US2018/035901 dated Oct. 16, 2018.
(Continued)

*Primary Examiner* — Neil N Turk
(74) *Attorney, Agent, or Firm* — Merchant & Gould P.C.

(57) ABSTRACT

Systems, including methods and apparatus, for growing viable monoclonal colonies, identifying them as monoclonal after their viability has been demonstrated, and picking and placing them into a target environment. The methods may include plating cells at low density in a well, capturing at a first time shortly after plating a series of vertically spaced-apart images of the well showing locations of the cells, capturing at a second, later time images of the same well showing locations of candidate cell colonies, determining a likelihood that the candidate colonies are monoclonal based on information in the first set of images, and, based on the likelihood, picking candidate colonies using a picking head for transfer to a target environment.

41 Claims, 7 Drawing Sheets

(51) Int. Cl.
*G01N 21/17* (2006.01)
*G01N 21/64* (2006.01)
*G06T 15/00* (2011.01)
*G06T 15/08* (2011.01)

(52) U.S. Cl.
CPC ..... *G01N 21/6452* (2013.01); *G01N 21/6456* (2013.01); *G06T 15/08* (2013.01); *G01N 2021/1782* (2013.01)

(56) References Cited

OTHER PUBLICATIONS

European Extended Search Report in Application 18808719.1, dated Feb. 4, 2021, 9 pages.
PCT International Preliminary Report on Patentability in Application PCT/US2018/035901, dated Dec. 12, 2019, 10 pages.

CELL COLONY PICKING SYSTEM

CROSS-REFERENCE TO PRIORITY APPLICATION

This application is a U.S. National Stage of International Application No. PCT/US2018/035901, filed Jun. 4, 2018, which claims the benefit under 35 U.S.C. § 119(e) of U.S. Provisional Patent Application Ser. No. 62/514,747, filed Jun. 2, 2017, each of which is incorporated herein by reference, in its entirety, for all purposes.

CROSS-REFERENCES TO OTHER MATERIALS

The following U.S. patent is incorporated herein by reference, in its entirety, for all purposes: U.S. Pat. No. 7,776,584.

INTRODUCTION

Automated devices for screening and selecting cell colonies have been commercially available for several years. However, current systems have a number of shortcomings. In particular, these systems are ill-suited for identifying and picking monoclonal colonies (i.e., colonies derived from a single cell). Yet, because the cells in monoclonal colonies are genetically identical, such colonies are important in both research and industry. Currently, monoclonal colonies are produced using multiple steps and instruments. For example, single cells are first isolated using techniques such as fluorescence-activated cell sorting (FACS). Next, these single cells are plated, preferably one cell to a well, in high-density multiwell plates. Finally, the cells are grown into colonies. This involves the use of large quantities of reagents and large numbers of multiwell plates. Moreover, the viability of cell colonies produced in this way is low.

SUMMARY

The present disclosure provides systems, including methods and apparatus, for growing viable monoclonal colonies, identifying them as monoclonal after their viability has been demonstrated, and picking and placing them into a target environment. The methods may include plating cells at low density in a well, capturing at a first time shortly after plating a series of vertically spaced-apart images of the well showing locations of the cells, capturing at a second, later time images of the same well showing locations of candidate cell colonies, determining a likelihood that the candidate colonies are monoclonal based on information in the first set of images, and, based on the likelihood, picking candidate colonies using a picking head for transfer to a target environment.

DETAILED DESCRIPTION

The present disclosure provides systems, including methods and apparatus, for growing viable monoclonal colonies, identifying the colonies as monoclonal after their viability has been demonstrated, and picking and placing them into a target environment. Significantly, the methods may involve first growing viable monoclonal colonies and then, after proving viability, identifying or confirming the colonies as monoclonal. In contrast, current technologies involve first isolating single cells, which are monoclonal by definition, and then attempting to cultivate the isolated cells into viable colonies. These current technologies are manually intensive and time consuming, generally involving several steps that include placing single cells per well in 96-well plates. Moreover, with current technologies, cell viability is poor (typically less than 40% survival rate), and large quantities of reagents and large numbers of multiwell plates are required to obtain a desired number of monoclonal colonies (e.g., 400 plates to harvest 10,000 colonies). Further aspects of the present disclosure are described in the following sections: (I) overview of methods, (II) overview of apparatus, and (III) examples.

I. Overview of Methods

FIGS. 1-4 are flowcharts showing an exemplary method for generating monoclonal cell colonies. Most or all of the steps associated with the method are performed on an initial day, termed "Day Zero" or "Day 0," when cells are plated, and on a final day, termed "Pick Day," when monoclonal cell colonies are picked and transferred. In brief, these steps include imaging cells on Day Zero and imaging cell colonies on Pick Day. Comparison of these images allows users to ascertain whether colonies selected on Pick Day correspond to single cells imaged on Day Zero (i.e., whether all of the cells in the colony are monoclonal because they arose from a single originator cell). Details of the method are described below.

A. Day Zero Activities

Figure 1:
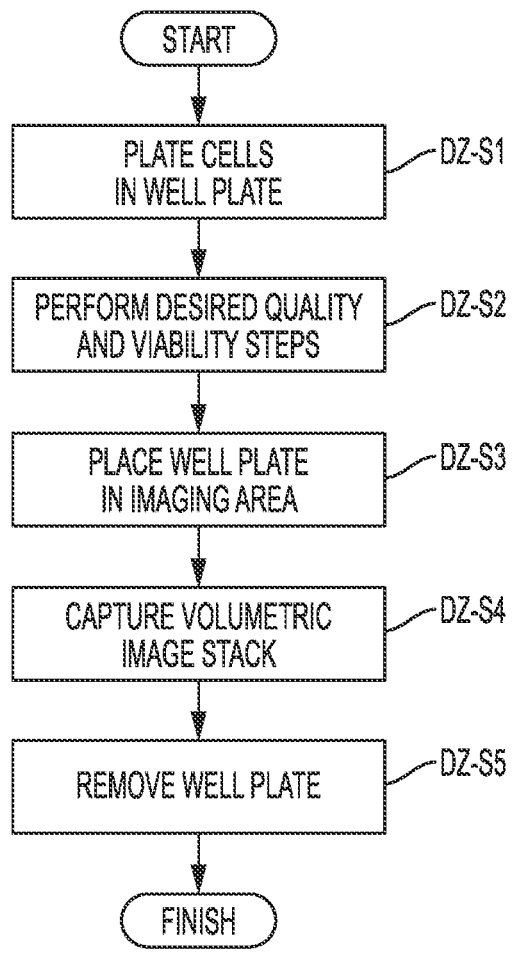
FIG. 1 is a flowchart depicting exemplary Day Zero steps in an illustrative method for identifying and picking monoclonal cell colonies.

Day Zero activities include plating cells, performing manipulations, as desired, to promote the cells' uniform spatial distribution and subsequent growth, and capturing the cells' Day Zero locations; see FIG. 1. Wells may be stored in an incubator between Day Zero steps.

Step DZ-S1. Cells of interest and a suitable growth medium are combined and added to a sample well, in a process termed "plating." The well generally comprises any suitable container for holding the cells and support material. Typically, the well will be one of a plurality of wells in a sample plate, such as a tissue culture plate, a microplate, or other multiwell plate. The well(s) may have a transparent base that allows contents of the well to be viewed and imaged from below. Alternatively, or in addition, contents may be viewed and imaged from above. Normally, cells and growth medium are loaded into all the wells of a multiwell sample plate. The growth medium may be designed or selected to gel and/or otherwise increase its viscosity after being added to the well. Gelling may slow or stop movement of cells and cell colonies and thus facilitate tracking their locations over time; however, it does not prevent cells from dividing. Gelling ideally occurs quickly relative to characteristic times required for cell division, for example, within about 6 hours, about 4 hours, about 2 hours, about 1 hour, or about 30 minutes, among others. Otherwise, cell division may make it impossible to distinguish two unrelated cells in proximity from two monoclonal cells derived from a single cell at that location that has undergone cell division. Suitable growth media include commercially available semi-solid matrix (SSM).

Step DZ-S2. Various follow-up steps may be performed to promote quality plating and subsequent cell viability. For example, sample wells may be centrifuged to accelerate cell movement (settling) toward the bottom of the well. In some embodiments, additional medium may be added after this step, ensuring that most or all cell colonies will be located in the bottom portion of the well, while also providing additional medium to promote cell growth and viability. In the same or other embodiments, wells may be covered with an air-permeable seal or other cover to protect well contents and prevent evaporation. These steps are explored further in Example 3.

Step DZ-S3. The well or sample plate may be placed or otherwise loaded onto an apparatus having an imaging system, such as a digital imaging system, and a mechanism, such as a table or stage, for supporting the well. This step typically is performed after the support material has gelled, to avoid jostling cells, and before imaging (see below). Images in this and other imaging steps may be created and stored in any suitable format.

Step DZ-S4. A plurality of vertically spaced-apart images of the well may be captured, using a digital imaging device. These images may be taken at different Z heights through the well, or more specifically through the growth medium-containing portion of the well, generating a volumetric image stack (which may alternatively be termed a Z stack). The volumetric image stack may be likened to a deck of cards, with individual cards representing individual images, and the set of cards representing the image stack. Continuing the analogy, the perpendicular running between the top and bottom of the deck represents the Z (vertical) direction, and the plane of the cards represents the XY (horizontal) direction. In some cases, depending on both well size and details of the imaging device, the imaging device may capture a horizontal slice through the entire well. However, more commonly, especially with large wells, the imaging device will capture only a portion of the XY plane through the well. In this case, a plurality of horizontally offset images may be captured at each Z height and then these images may be tiled (abutted) or stitched (overlapped) together to cover a larger horizontal area of the well. The purpose of the image stack is to be able to identify the initial locations of individual cells within the well for later comparison with colony locations. Further aspects of imaging, including light sources and detectors, are discussed elsewhere in the application.

Step DZ-S5. The well is removed from the apparatus after completion of imaging and stored (typically incubated) to allow colony growth.

B. Day 1 to Pick Day Minus 1 Activities

Wells are incubated from Day Zero to Pick Day under conditions favorable to cell growth. These conditions may include proper atmospheric composition, humidity, and temperature. The conditions also may include the provision of proper nutrients, buffers, cofactors, and the like. Viable cells will divide during this time to form colonies. For example, a typical doubling time for mammalian cells is 24 hours; therefore, on Day N, the cells from each originator cell will form a colony comprising roughly $2^N$ cells. Thus, under ideal conditions, cell colonies may contain about 1000, about 4000, and about 16000 cells on Days 10, 12, and 14, respectively.

Wells optionally may be imaged or otherwise analyzed between Day Zero and Pick Day. This optional imaging may include collecting planar images, showing part or all of a single horizontal section, or collecting volumetric images, showing an entire Z-stack. These intermediate time images can be used for any suitable purpose, including providing further historical evidence of cell locations, assessing the health of the colonies, deciding when to schedule Pick Day, and so on.

C. Pick Day Activities

Figure 2:
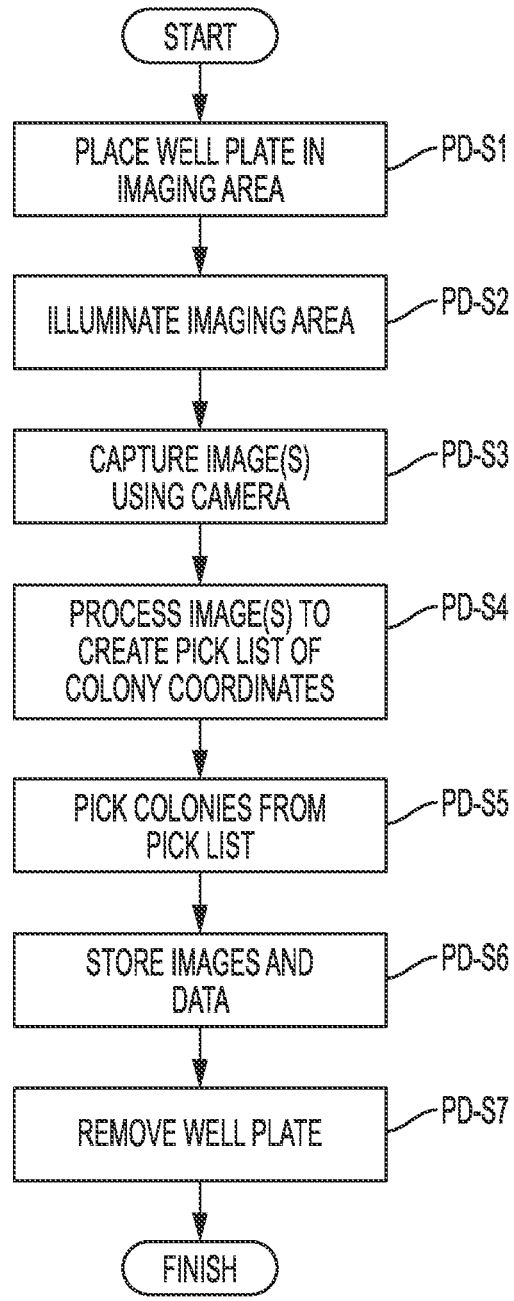
FIG. 2 is a flowchart depicting exemplary Pick Day steps in an illustrative method for identifying and picking monoclonal cell colonies.
Figure 3:
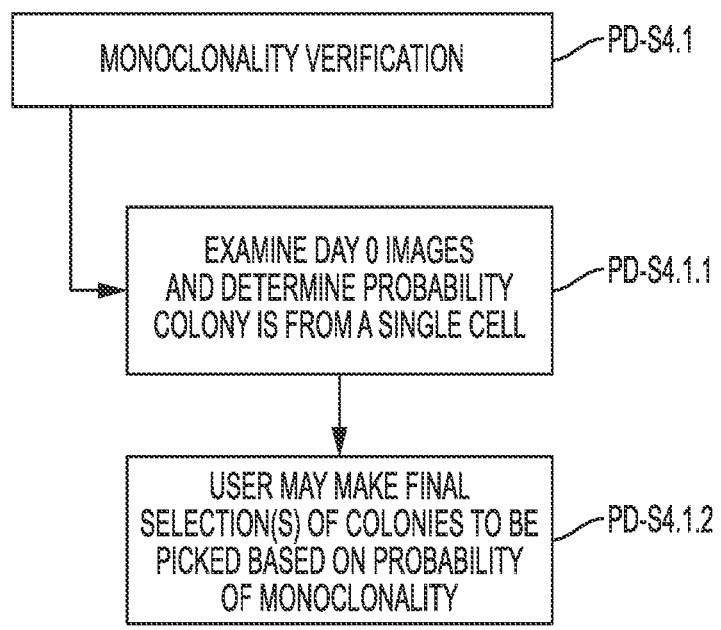
FIG. 3 is a flowchart depicting exemplary steps for confirming monoclonality, which may be performed in connection with the method of FIGS. 1 and 2, for example, as part of Step PD-S4 in FIG. 2.
Figure 4:
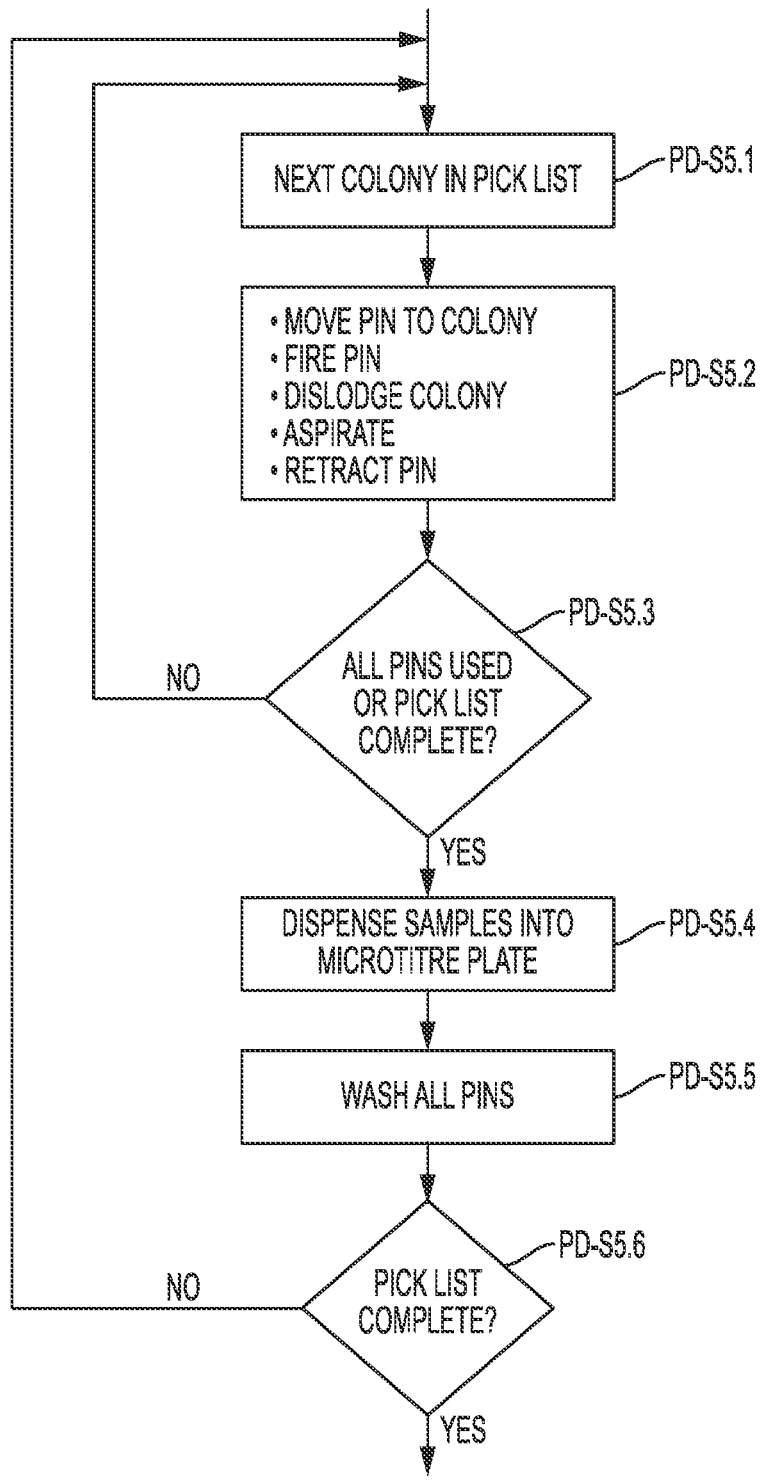
FIG. 4 is a flowchart depicting exemplary steps for confirming picking monoclonal colonies, which may be performed in connection with the method of FIGS. 1 and 2, for example, as part of Step PD-S5 in FIG. 2.

Pick Day activities include imaging colonies of cells, determining a measure of likelihood that the imaged colonies are monoclonal, creating a "pick list" of suitable colonies based on that likelihood, and picking and placing colonies on the list by physically retrieving at least a portion of each colony and placing it into a target environment; see FIGS. 2-4.

Step PD-S1. A sample plate containing candidate colonies may be placed in an imaging area. The imaging area may include a sample support, such as a table and/or stage, to hold and manipulate the sample plate during illumination and imaging.

Step PD-S2. The imaging area containing the sample plate may be illuminated using suitable light. This light may be provided via trans-illumination, directed from a light source through the sample to a detector, via epi-illumination, directed from the light source to the sample and from the sample back to the light source along the same path, and/or via side-illumination, directed from the light source to the sample from an angle off the axis from the sample to the detector. Illumination light may include white light or colored light, depending on the sample. White light is typically used for unstained colonies, whereas colored light is typically used for stained colonies. Illumination light also may be filtered or generated with specific colors for use in fluorescence assays.

Step PD-S3. The sample plate may be imaged, typically in a single plane, using the applied illumination. Images are captured using a digital imaging device, which may be the same as or different from the imaging device used to capture Day Zero images.

Step PD-S4. The captured images may be processed to identify candidate colonies and to assess the likelihood that the candidate colonies are monoclonal. The identification of candidate colonies may be performed using software that recognizes colonies due to their color, their light absorbance or reflectivity relative to background, and/or other properties. In some cases, cell colonies may be made visible using fluorescence. For example, a fluorescently labeled antibody may be used that binds to a protein of interest secreted from, expressed on the surface of, or contained within the cell colonies. During the fluorescence imaging, the cell colonies will appear as brightly emitting spots when illuminated with an appropriate excitation wavelength. Depletion of the fluorescent antibody in the immediate vicinity of the cell colonies may also occur, which has the additional benefit of producing an "inverse halo" (i.e., a darker area around each bright colony that aids the image processing). Alternatively, in the case of staining, the cell colonies may be made visible by mixing a suitable stain into the medium. Finally, many colonies can be identified without fluorescence or staining. The locations of colonies further satisfying the monoclonal selection criteria, as described below in connection with FIG. 3, are compiled into a pick list of colony coordinates.

Step PD-S5. Cells from colonies on the pick list are next picked up, or collected, using a robotic device and transferred to a new environment, typically in another sample plate. Colony picking is further described below, in connection with FIG. 4.

Step PD-S6. Images and other data are stored for future reference.

Step PD-S7. Sample plates containing the picked colonies are removed for further growth and/or analysis.

FIG. 3 is a flowchart showing further aspects of Step PD-S4, relating to colony selection and generation of a pick list. Each of the candidate colonies is subjected to a secondary analysis in which Day Zero images are examined and a probability that the colony is derived from a single cell is estimated. In other words, the identification of colonies as monoclonal is made by correlating the position of the colony in a Pick Day image with the position of a single originator cell in a Day Zero image. This involves making certain assumptions about cell movement, which can be expressly confirmed, if desired, with images taken from Day 1 to Pick Day Minus 1. Cells tend to drift or otherwise move downward through the medium over time. The majority of this movement happens shortly after plating because the viscosity of the semi-solid medium generally increases with time. Accordingly, there typically is a delay between plating and imaging on Day Zero. This allows a better determination of Day Zero locations and thus a better determination of the origins of cell colonies on Pick Day (e.g., 10 to 14 days later). Nevertheless, cells can continue to move, typically downward, even if the medium has gelled. The distribution of possible positions corresponding to a given starting position forms an inverted cone, with its apex at the starting position. When candidate colonies are identified on Pick Day, additional analysis is performed to confirm monoclonality based on the volumetric image stack generated on Day Zero. For example, it may be determined that only a single cell has a cone of probable locations that intersects a hemisphere defined by a selected radius centered on the candidate colony, in which case there would be a high likelihood of monoclonality. The user makes a final selection of which colonies to pick using the measure of likelihood that the colony is monoclonal. In some cases, this choice may be informed by re-examination of supporting images from Day Zero and, if multiple time-point tracking is employed, later days.

FIG. 4 is a flowchart showing further aspects of Step PD-S5, relating to cell colony picking. Step PD-S5 has several sub-steps. In PD-S5.1, a colony is selected from the pick list for picking. In PD-S5.2, a pin or other retrieval device is moved to the assigned XY coordinates of the cell colony to be picked. The pin is "fired" (i.e., lowered) to colony picking position with the end of the pin introduced into the medium over the target cell colony. If the colony is adherent, the end of the pin may be agitated to dislodge the target cell colony. Next, the pin aspirates or otherwise picks up a defined volume of medium that includes part or all of the target colony. Finally, the pin is retracted and the sample retained. In PD-S5.3, a determination is made whether to repeat the picking process with another colony and another pin, which will occur unless all of the pins have been used or all of the colonies in the pick list have been collected. In PD-S5.4, the picked colonies are dispensed into a target environment, for example, a multiwell plate. Dispensing may occur serially (one target well at a time) and/or in parallel (multiple target wells at the same time, which can occur if the pins and the target wells have the same footprint). In PD-S5.5, the pins are either replaced or, more commonly, cleaned and dried for further use. In PD-S5.6, a determination is made whether to repeat steps PD-S5.1 through PD-S5.5, which will occur unless all colonies in the pick list have been collected and transferred. Suitable apparatus and further details for performing Step PD-S5 are described in U.S. Pat. No. 7,776,584.

II. Overview of Apparatus

Figure 5:
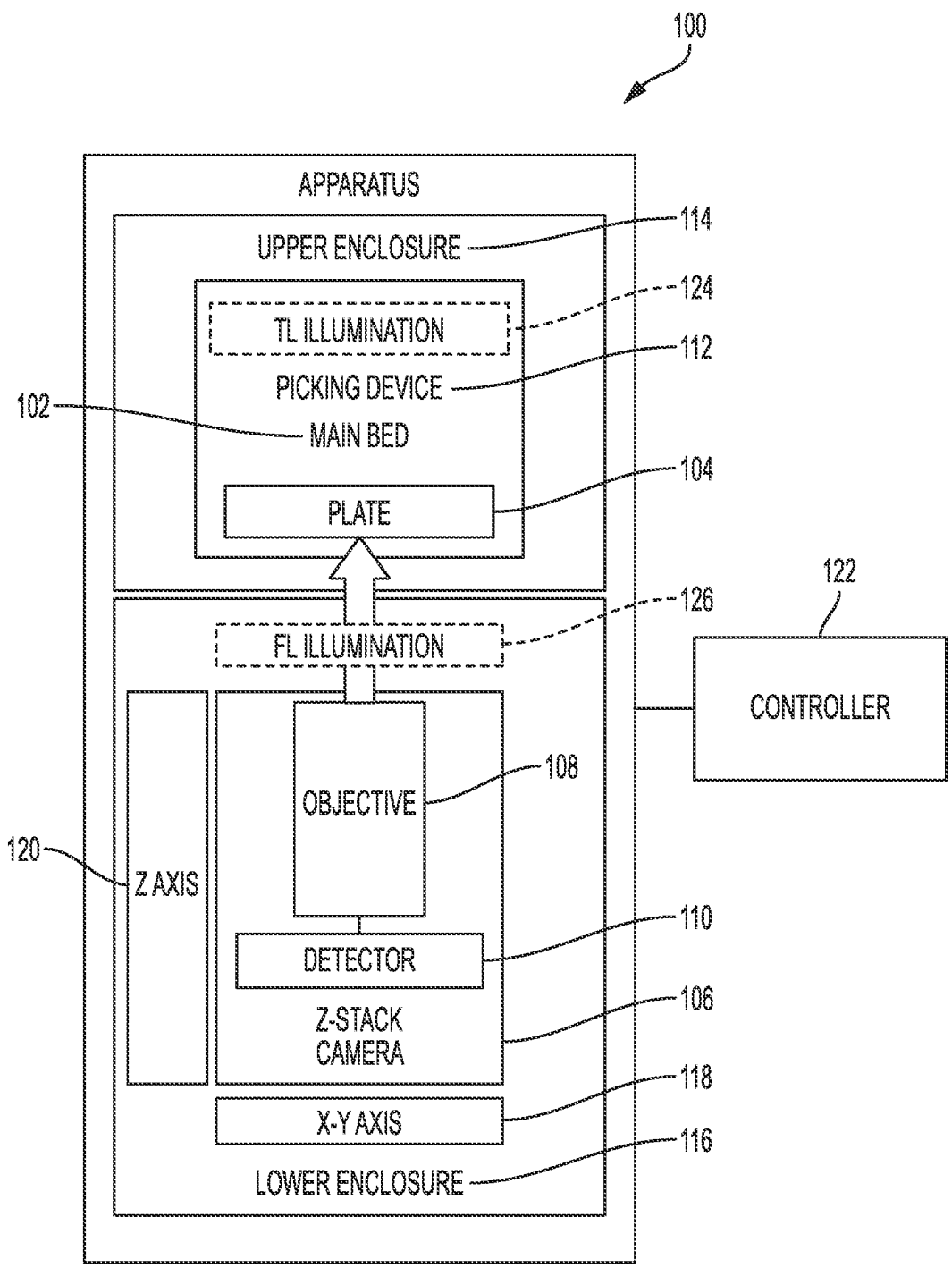
FIG. 5 is a highly schematic view of an exemplary apparatus for identifying and picking monoclonal cell colonies
Figure 6:
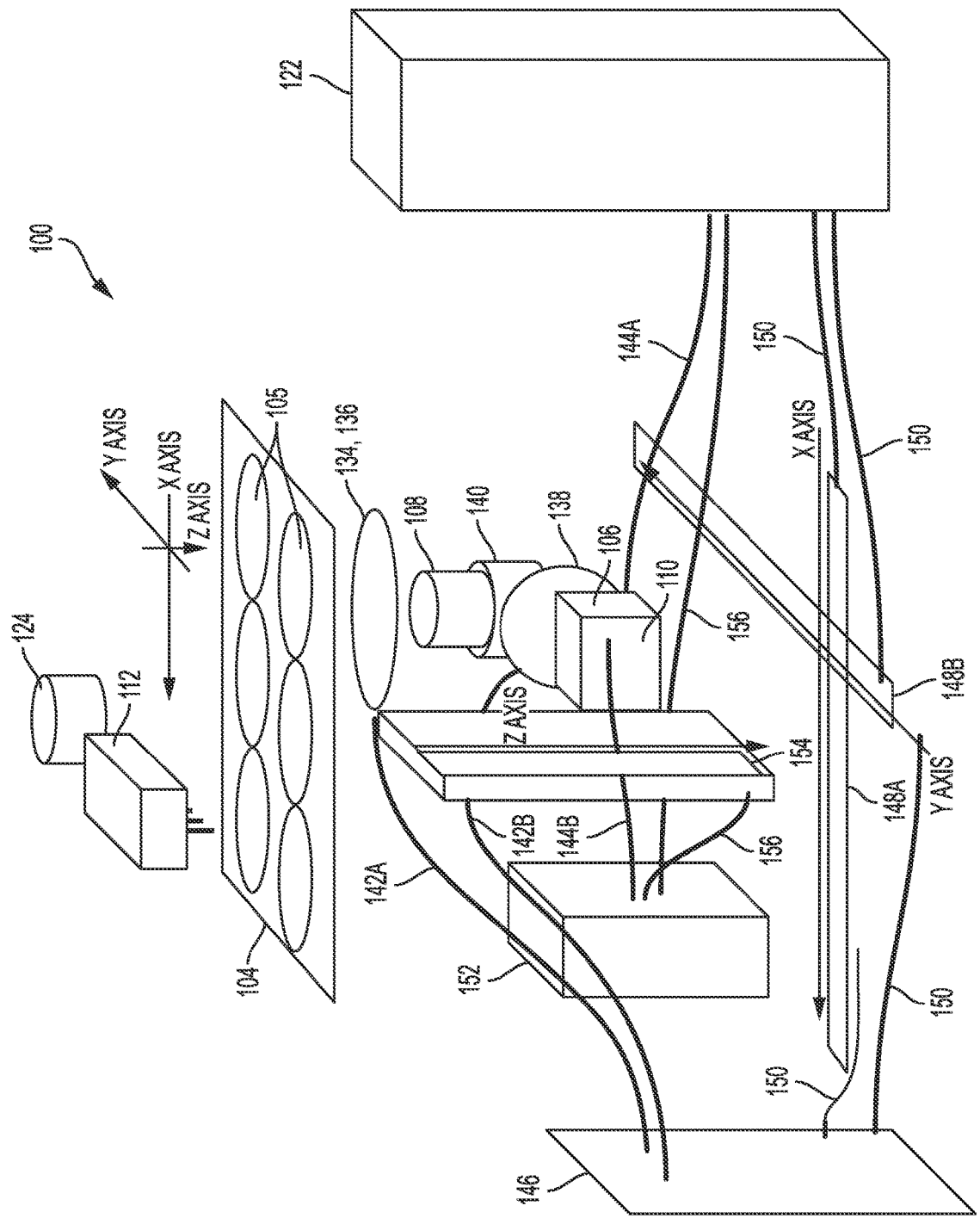
FIG. 6 is a less schematic view of portions of the apparatus of FIG. 5.
Figure 7:
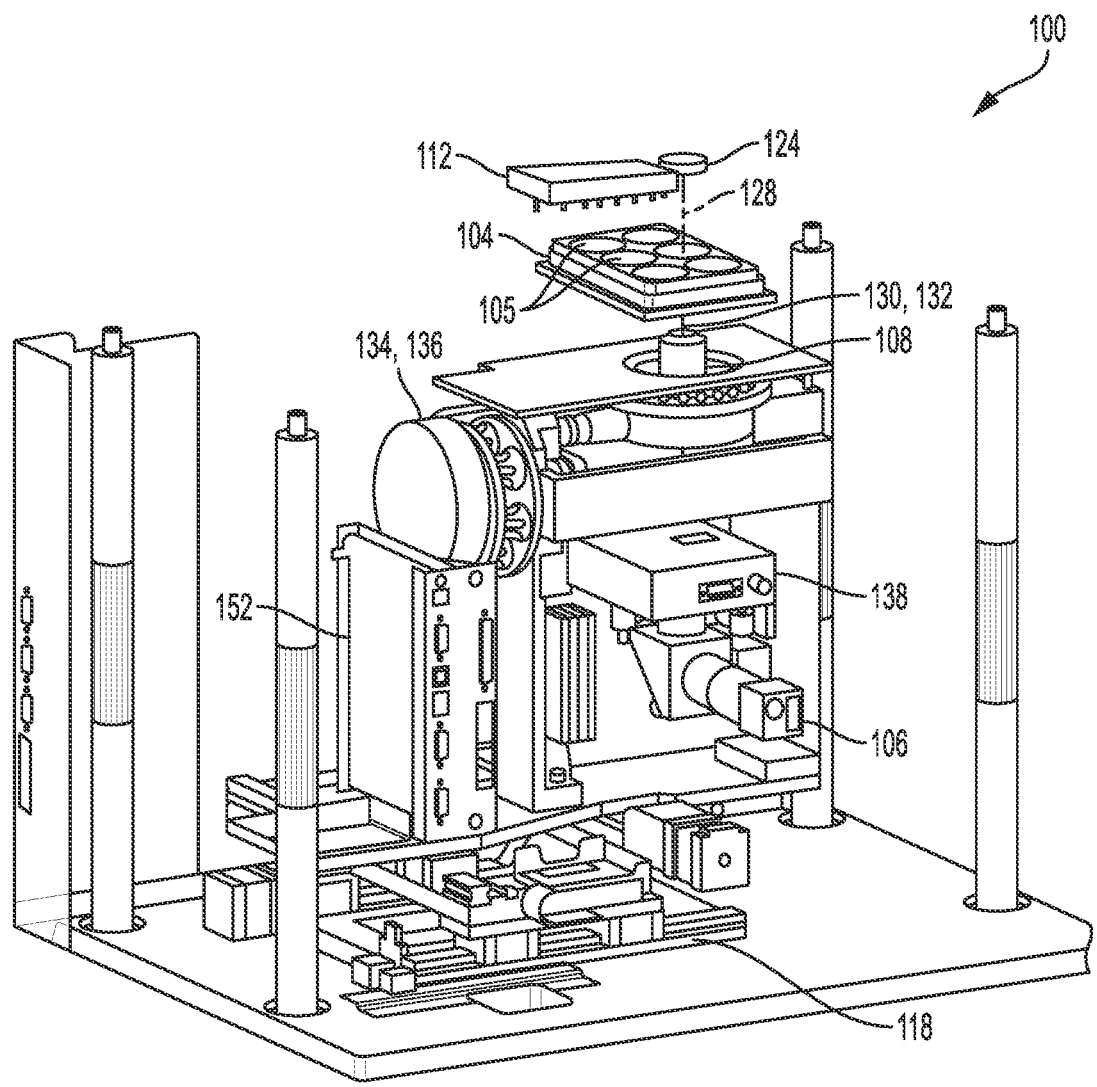
FIG. 7 is an isometric view of the apparatus of FIG. 6.

FIGS. 5-7 show an exemplary apparatus 100 for identifying and picking monoclonal cell colonies. The apparatus may include a main bed or table 102 for supporting a multiwell plate 104, with sample wells 105, over a digital imaging device (i.e., a camera) 106 comprising an objective 108 and a detector (e.g., a CCD camera, a CMOS camera, etc.) 110 for capturing images of the contents of the wells. Main bed 102 and a cell picking device 112 mounted thereon may be covered by an upper enclosure 114. The picking device may include pins (shown as vertical projections from cell picking device 112) for engaging and picking up portions of a cell colony. In some cases, the pins may be hollow, allowing them to "suck up" a portion of a colony and then "squirt" it into a destination well or other location. A base of the apparatus may house the camera in a lower enclosure 116. The upper enclosure and lower enclosure collectively may form a housing. The objective, or entire camera, may be mounted on an X-Y-axis stage 118 and/or a Z-axis stage 120, for three-dimensional positioning. In some embodiments, the camera may take multiple coplanar images, and those images may be stitched or tiled together to form a single image. In the same and/or other embodiments, the camera may capture further images at various Z-heights. A controller or controllers 122 may be in communication with the apparatus, and may be used to coordinate and control camera activity, as well as cell-picking and machine vision activities. Various illumination devices may be utilized to light the well plate region for imaging. For example, white-light trans-illumination 124 and/or fluorescence epi-illumination sources 126 may be used. The apparatus may further include accessible fluidics station for supplying appropriate media and reagents. Further aspects of a suitable apparatus are described in U.S. Pat. No. 7,776,584.

FIGS. 6 and 7 show further details of the illumination system. Trans-illuminator 124 may be positioned above the sample well and produce light 128 that travels through well 105 and the associated cells and medium and into objective 108 to detector 110. Epi-illuminator 126 may be positioned below the sample well and produce fluorescence excitation light 130 that travels upward through well 105, exciting fluorescence emission light 132 from selected colonies in the well, some of which then travels downward through the well and into objective 108 to detector 110. Epi-illuminator 126 may further include a light source 134, fluorescence excitation filters (if appropriate) 136, fluorescence emission filters 138, and optics (e.g., mirrors and lenses) 140 for directing light from the light source to the well and from the well to the detection device. Light sources, camera(s), filters, and/or other optics may be under electronic control via suitable wired or wireless connections 142A,B and triggers 144A, B.

FIGS. 6 and 7 also show further details of the X-Y-Z stages and controllers. X-Y (horizontal) and Z (vertical) motion may be supported and controlled separately. For example, X-Y movement and position may be controlled by an XY axis controller 146, an X-axis encoder 148A, a Y-axis encoder 148B, and various X-Y-axes control lines 150. Similarly, Z movement may be controlled by a Z-axis controller 152, a Z-axis encoder 154, and various Z-axis control lines 156.

EXAMPLES

The following examples describe selected aspects and embodiments of the present disclosure, including exemplary work flows and exemplary methods of producing monoclonal colonies. Imaging, analysis, and picking of cell colonies may be performed in one apparatus. The positions of originator cells are recorded at the beginning of colony growth. This position information is later used in assessing the likelihood that candidate colonies are monoclonal. The examples are presented for illustration only and are not intended to define or limit the scope of the present disclosure.

Example 1. Exemplary Instrument/Software Workflow

This example describes an exemplary instrument/software workflow. In general, software/instrument workflows, such as that described here, should interleave with biological workflows (see, e.g., Examples 4 and 5 below).
A. Day Zero.

"Day Zero" occurs shortly after plating and includes the initial three-dimensional image capture in the X, Y, and Z planes. Three-dimensional image capture, on Day Zero or later, typically employs transmitted white light (WL). A six-well plate (or other suitable plate) is inoculated with cells. Shortly afterwards, the plate is placed in the instrument. To ascertain initial individual cell positions, volumetric imaging is used to capture Z stacks of images at suitable vertical intervals over the six wells. Capture performance, including the number of images and the distance between them, will depend on the depth of the medium, the exposure time, and any experiment-specific criteria. The time required for image capture may vary, but in general should be less than about 45 minutes per plate. For example, collecting images every 30-35 µm, capture times can be less than about 30 minutes for plate. Images will be stored, typically in twelve-bit gray scale in jpeg format, for use when qualifying colonies as monoclonal for picking.
B. Planar Imaging.

Planar imaging may be performed at any time of interest using transmitted light (WL) or fluorescence (FL) illumination. Images are be taken in the same plane, or planes, at or near the bottom of the plate, over six wells. Each well is covered by 100 to 140 images, depending on the exclusion zone(s). Images are tiled or stitched into a cohesive view of the plate.
C. Pick Day.

Pick Day imaging is performed using planar imaging, as described above, typically using FL illumination. Images are stored, typically in twelve-bit gray scale, for analysis when verifying candidate colonies for picking. Monoclonal colonies may be selected using a two-stage process. Stage 1 comprises identifying colonies of interest in the Pick Day image(s). Identification criteria may include size, morphology, the ease with which the colony can be retrieved with a picking head, and so on. Stage 2 comprises assessing the likelihood that colonies identified in Stage 1 are monoclonal. For each candidate colony, this involves reviewing regions of the Day Zero images showing the area (or volume) near the candidate colony and application of suitable monoclonality criteria, such as where there was a single cell on Day Zero at or near the position of the colony and whether any other cells were sufficiently close to that cell to have started colonies that could have fused with and thus contaminated the candidate colony. Users may make a final selection based on Stage 2 probabilities and supporting images. After final selection, colonies may be picked and transferred from source wells to suitable destinations, for example, following the process described in U.S. Pat. No. 7,776,584.

Example 2. Exemplary Throughput and Storage Calculations

This example describes a hypothetical scenario to illustrate throughput and storage requirements for the disclosed methods.

Throughput Calculation.

Suppose that the depth of growth medium in a well is 1 mm and that images for a Z-stack are collected at 50 µm intervals. These conditions will produce a total of about 20 images. The exposure per image is set at 5 ms. To limit image blur, the distance covered by a moving camera during an exposure should be less than or equal to 2 µm. This condition can be achieved by moving the camera at a constant velocity of 0.4 mm/sec. Thus, Z travel time over 1 mm is 2.5 seconds. Adding (motion overhead) 1.5 seconds per transit to next frame yields 4.0 seconds per volumetric image stack. Assuming that 100 volumetric image stacks are collected per well, the total time required to image a six-well plate will be about 40 minutes.

Storage Calculation.

Acceptable image quality can be obtained using a 2048-by-2048 camera, with eight bits per pixel. This corresponds to 4 MB per image, 80 MB per volumetric image stack, and 48 GB per six-well plate. The required data throughput is 32 MB/second, on average.

Alternative Embodiments

The calculations above are intended to show that the methods for creating monoclonal colonies described herein have relatively modest throughput and storage requirements. Moreover, these requirements may be reduced even further under relatively standard conditions. For example, by collecting images over a smaller vertical height (e.g., 0.8 mm) and by reducing exposure time (e.g., to 1-3 ms), total frame time can be reduced to about 2.2 seconds per volumetric image stack and about 25 minutes per plate. Similarly, by using suitable image compression (e.g., JPEG compression), storage sizes can be reduced (e.g., to less than about 10 MB per volumetric image stack, even for twelve-bit grayscale images separated by about 35 µm per image).

Example 3. Exemplary Method to Create Monoclonal Colonies

This example describes exemplary methods to create monoclonal colonies. The methods may include imaging, analysis, and picking of cell colonies in one instrument through the whole process. The methods may result in high cell viability in six-well plates and/or the use of fewer (e.g., 10-25) plates. Significantly, as noted elsewhere, the methods may involve first growing viable monoclonal colonies and then, after establishing their viability, identifying or confirming the colonies as monoclonal, Selected colonies may then be picked and placed into a target environment.

A. Introduction

The behavior of cells plated in a semi-solid medium is an important determinant of both hardware and software requirements. This example summarizes observations of the XYZ (three-dimensional) motion of cells plated in semi-solid medium. These observations are used to suggest and assess potential workflow improvements that may reduce such XYZ motion, which in turn may improve the ability to assess monoclonality by facilitating correlation of the positions of candidate cell colonies and their single originator cells.

B. Materials and Methods

Cell Line.

CHO-S(Chinese Hamster Ovary).

Semi-Solid Media.

CloneMedia CHO Growth A, with L-Gln (L-Glutamine) (Molecular Devices K8810).

Plating and Culture Conditions.

Unless otherwise stated, cells were plated in 2 ml/well semi-solid medium (prepared according to product data sheet) in Greiner 6-well culture plates with 4 ml $H_2O$ in the central plate reservoir. Immediately following addition of media/cells, plates were centrifuged at 100×g for 5 minutes. The semi-solid medium preferably is viscous enough to stabilize cell position, yet optically transparent enough to allow top-to-bottom visualization and imaging.

Multiwell Plates.

Cells can be grown in any suitable container. Six-well plates are well-suited to the combination of growth, imaging, and picking.

Imaging:

Unless otherwise stated, all imaging was performed on either a Molecular Devices ImageXpress Micro C high-content imaging system (IXM-C) or a Molecular Devices ImageXpress Micro 4 high-content imaging system (IXM-4) with a 4×/0.2NA Plan Apo objective lens. Image Z-stacks were taken at each imaging site, with 50 μm gaps between planes. Suitable combinations of camera, camera/plate positioning, and optical path allow clear imaging of single cells and differentiation between cells and debris.

C. Findings

The following results were obtained using a CHO lineage cell line. Differences in cell type, incubator age/function, and user may have an impact on the findings.

Data Summary Table. Refer to text for details.

| Media Volume | | 2 ml | 1 ml (w/wo seal) | 1 ml (+1 ml layer) |
|---|---|---|---|---|
| number of cells measured | | 1066 | 377 | 247 |
| cells located at well bottom | | 80-100% | 100% | 95-98% |
| average distance moved (um) | cells at well bottom | 90 | 110 | 85 |
| | cells in high Z | 840 | n/a | 710 |
| min/max movement (um) | cells at well bottom | 5/350 | 5/300 | 1/275 |
| | cells in high Z | 180/1350 | n/a | 170/1500 |

(i) Plating of Cells in Semi-Solid Medium Under Standard Conditions Makes it Extremely Difficult to Correlate Colonies Back to their Originator Cells A static imaging time-lapse analysis of cells (n=46 cells) plated under standard conditions (see Methods above; 2000 cells/ml), performed over the first 24 hours after plating, demonstrated that only ~70% of cells were located within 50 μm of the well bottom at time 0. The remaining 30% of cells were distributed throughout the media volume; these cells settled to the well bottom during the first few hours (100% of cells at 8 hours). Of the cells at the well bottom, an average of 90 μm XY (horizontal) movement was observed over the first 12 hours, with a range of 5-170 μm. Of the cells distributed higher in the media, an average of 400 μm XY motion was observed, with a range of 250-520 μm. After 12 hours, only minor XY shifts were observed, suggesting that the media had gelled sufficiently to prevent significant motion of the cells.

Under non-static (dynamic) imaging conditions, which involve plate transfers between the incubator and instrument and movement of the imaging stage during image capture (n=1066 cells, 3 individual experiments, Day Zero imaging ranged from 2-8 hours post-plating), an average of 85% of cells were located within 50 μm of the well bottom after 2 hours. The remaining 15% of the cells were distributed throughout the media. The majority of these cells settled to the well bottom over the next few hours. However, variation was observed between the experiments; 80% to 100% of the cells were observed to be on the well bottom after 24 hours. Of the cells located at the well bottom, an average of 90 μm XY movement was observed over the first 24-48 hours, with a range of 5-350 μm. Of the cells distributed higher in the media, an average of 840 μm XY motion was observed, with a range of 180-1350 μm. These large XYZ motions (spatial displacements) make it hard to associate colonies with their originator cells. In addition, there is a possibility for moving cells to merge with other colonies undetected; therefore, even if a colony is shown to have originated from a single cell observed on Day Zero, the certainty of monoclonality is reduced due to the possibility that colonies originating from moving cells have merged.

Potential solutions to avoid large XYZ displacements after Day Zero imaging would be to increase the time period between cell plating and Day Zero imaging, thereby allowing the maximum number of cells to reach well bottom, or to speed up this settling process by increasing centrifugation speed or time.

For the former, a minimum of 8 hours would be recommended between plating and imaging to allow for as many cells as possible to settle. However, variability between experiments has shown that 8 hours may not be sufficient; up to 20% of cells may still experience large XYZ displacement after this time. In addition, 8 hours after plating, ~30% of cells will have divided and therefore will later be disqualified as colonies of interest due to uncertainty of monoclonality. This exclusion of a large population of cells would significantly reduce throughput. In addition, significant delays between plating and imaging can have labor and resource consequences, because the Day Zero workday could potentially extend to 16 or more hours (timing based on 10 plates, estimate of 45 minutes imaging per plate).

For the latter (increased centrifugation), an increase in centrifugation from 5 minutes at 100×g to 10 minutes at 100×g resulted in no difference in the cell Z distribution on Day Zero. Therefore, XYZ displacement was still significant. Further exploration of centrifugation speeds and time may improve this result; however, investigation of this increased centrifugation's effect on cell viability would also be required.

In summary, large XYZ displacements of cells under standard conditions (2 ml/well) resulted in poor correlation of colonies back to their originator cells, thereby reducing certainty of monoclonality.

(ii) Reduction of Media Volume Reduces Cell XYZ Movement, Thereby Allowing Easier Tracing of Colonies Back to their Originator Cells An investigation was undertaken to determine if the Z-coordinate distribution of cells could be reduced. Cells were plated as described above, except here the volume of medium per well was reduced from 2 ml to 1 ml and the concentration of cells was increased to 4000 cells/ml. A static imaging time-lapse analysis of cells (n=56 cells) demonstrated that 100% of cells were located within 50 μm of the well bottom at time 0. An average of 40 μm XY motion was observed over the first 12 hours, with a range of 8-101 μm. After 12 hours, only minor XY shifts were observed, suggesting that the media had gelled sufficiently to prevent significant motion.

Under non-static (dynamic) imaging conditions, which involved plate transfers between the incubator and instrument and movement of the imaging stage during image capture (n=377 cells, 3 individual experiments, Day Zero imaging ranged from 3-8 hours post-plating), 100% of cells were located within 50 μm of the well bottom on Day Zero. An average of 110 μm XY movement was observed over the first 24-48 hours, with a range of 5-300 μm. These limited XYZ displacements allow much easier tracing of colonies to their originator cells on Day Zero. In addition, the low cell concentrations required for optimal colony spacing for picking decrease the chance of cells merging in a single colony as nearest neighbors will generally be separated by >0.5 mm.

In summary, reduced Z distribution of cells with reduced media volume (1 ml/well) will result in reduced XYZ displacements. This facilitates correlation of colony positions with originator cell positions, making certainty of monoclonality high if a single cell is visible on Day Zero in proximity to a candidate colony, with no other cells in proximity.

(iii) Reduction of Media Volume has a Negative Impact on Cell Viability and Growth The reduced media volume per well provides a solution to the difficulties associated with matching the positions of originator cells and colonies, and therefore increases certainty of identification of monoclonal colonies. However, reduced media volume has an impact on colony health and growth.

1 ml of media placed in a well forms a very thin layer over the well surface, making cells much more prone to dehydration than with the larger media volume of 2 ml. Media on Day 5 looks visibly dry; the media layer is much thinner, and its appearance/texture visibly changes from the well center towards the edge. Colonies have different morphologies (shapes) when grown in 1 ml and 2 ml of medium. In addition, colonies are smaller at the reduced volume (60% of 2 ml size on Day 6, 45% on Day 8). These data suggest that the reduced media volume is having a detrimental impact on cell health.

In summary, although certainty of identification of monoclonal colonies is improved by reducing media volume per well, cell health is negatively impacted, which in turn negatively impacts the survival rates of clones of interest.

(iv) Potential Solutions are Available to Mitigate Cell Viability Issues Resulting from Reduced Media Volume Per Well A number of options are available to mitigate media dehydration and its impact on cell health. These include the addition of extra media after plating and the use of breathable plate seals.

Extra Media.

Investigations into addition of media (either semi-solid or liquid) after several days' growth were not successful; cells and colonies were disrupted by the additional media resulting in large XYZ displacement of cells, thereby reducing the ability of tracing colonies back to single originator cells.

An alternative to addition of extra media after several days is addition of extra media on Day Zero, before the initial imaging run. For this purpose, cells were plated in 1 ml of semi-solid medium and centrifuged for 5 minutes at 100×g. After waiting 30 minutes to allow the majority of cells to reach the well bottom, an additional 1 ml of CloneMedia media was carefully added to the top layer, by dripping down the well edge, before an additional 5 minute centrifugation step. Cells were imaged on Day Zero, approximately 3 hours after initial plating, and on Day 2. In control wells (1 ml media only; n=107 cells), 100% of cells were on the well bottom on Day Zero and had an average XY displacement of 90 μm (range 10-190 μm). For cells in the test wells (1 ml media/cells, 1 ml media layered on top; n=247 cells, 2 individual experiments), approximately 95% of cells were located at the well bottom on Day Zero with an average XY displacement of 85 μm (range 1-275 μm). Of the 5% of cells distributed higher in the media, average XY displacement was 710 μm (range 170-1500 μm). These XY distance values are similar to those observed with 2 ml media per well. However, the percentage of the cell population exhibiting this motion is significantly reduced in comparison, with only 5% of cells distributed high in the media instead of up to 20%. Therefore, the method of layering media on Day Zero both maintains the media hydration levels, and therefore cell health, and reduces (but does not eliminate) the risk of misidentifying monoclonal colonies compared to standard plating conditions.

Plate Seals.

Plate seals provide another mechanism for reducing media dehydration. There are a number of plate seals available commercially that are gas permeable and sterile. Using one of these breathable seals (USA Scientific Breathe-Easy seal) appeared to reduce the dehydration of media dispensed at 1 ml/well compared to plates without sealing. However, although the breathable seal improved colony growth compared to plate sealing, colony growth was still impaired compared to colonies in 2 ml of media; colonies in 1 ml (with seal) were 81, 71 and 67% the size of those in 2 ml on Days 9, 11 and 13 respectively. This difference in cell growth may be because of media dehydration below acceptable levels, or perhaps due to a lack of media nutrients given that the same number of cells is grown in half the volume of media and therefore nutrient supply will be consumed quicker. Although colony growth is slower with 1 ml media and a seal than with 2 ml media without a seal, colony morphologies are similar, with no visible signs of poor cell health, with outgrowth observed post-picking indicating that the cells are still viable. However, this result may not be applicable for different cell lines, given differences in their growth profiles and sensitivity to media conditions.

In summary, although there are still risks involved, we have demonstrated potential solutions for maintaining cell viability and growth with the reduced media volume of 1 ml. However, these solutions will require additional testing to define their domains of applicability.

Example 4. First Exemplary Biological Workflow

This example describes a first exemplary biological workflow.

Day Zero—Plate Cells.

Plate cells of interest in 1 mL semi-solid medium. Seal the plate with a breathable plate seal. Centrifuge the plate for 5 minutes at 100×g. Incubate the plate for a minimum of 2 hours in a humidified incubator.

Day Zero—Image Cells.

Capture plate images with transmitted light (WL). Collect planar images of plate wells at a series of heights, separated by a maximum of 50 µm, to form an image z-stack covering the entire volume of the semi-solid medium.

Days 4-14—Image Cells (Optional).

Image the plate, in one or more planes, with transmitted light (WL) to monitor growth.

Days 7-14—Image and Pick Cells.

Remove the plate seal. Image the plate, in one or more planes, using transmitted light (WL) and fluorescence light (FL). Select and pick colonies based on one or more user-defined criteria, including fluorescence intensity, morphology, and/or certainty of monoclonality.

Example 5. Second Exemplary Alternative Biological Workflow

This example describes a second exemplary alternative biological workflow.

Day Zero—Plate Cells.

Plate cells of interest in 1 mL semi-solid medium. Centrifuge the plate for 5 minutes at 100×g. Incubate the plate for 30 minutes. Carefully layer an additional 1 mL semi-solid medium over the existing semi-solid medium using the side of the well. Seal the plate, if desired, with a breathable plate seal. Centrifuge the plate for another 5 minutes at 100×g. Incubate the plate for a minimum of 2 hours in a humidified incubator.

Day Zero—Image Cells.

Image the plate with transmitted light (WL). Collect planar images of plate wells at a series of heights, separated by a maximum of 50 µm, to form an image z-stack covering the entire volume of the semi-solid medium.

Days 4-14—Image Cells (Optional).

Image the plate, in one or more planes, with transmitted light (WL) to monitor growth.

Days 7-14—Image and Pick Cells.

Remove the plate seal, if present. Image the plate, in one or more planes, using transmitted light (WL) and fluorescence light (FL). Select and pick colonies based on one or more user-defined criteria, including fluorescence intensity, morphology, and/or certainty of monoclonality.

Example 6. Selected Embodiments 1

This section describes further aspects and features of cell colony selection, analysis, and picking methods, presented without limitation as a series of paragraphs, some or all of which may be alphanumerically designated for clarity and efficiency. Each of these paragraphs can be combined with one or more other paragraphs, and/or with disclosure from elsewhere in this application in any suitable manner. Some of the paragraphs below may expressly refer to and further limit other paragraphs, providing without limitation examples of some of the suitable combinations. More generally, all suitable combinations are included. For example, paragraph A6, while referring to paragraph A0, can be combined with other preceding paragraphs, such as paragraph A5, or with subsequent paragraphs, such as paragraph A7, among others. Similarly, paragraphs in one family can be combined with paragraphs in other families. For example, paragraph A6 can be combined with paragraphs the B, C, and D families.

Paragraph A0. A method for selecting one or more monoclonal cell colonies using an apparatus having a digital imaging device, the method comprising: (a) loading a sample plate onto the apparatus, the sample plate including a well having a plurality of cells held in a semi-solid medium; (b) capturing, at a first time and using the digital imaging device, a first plurality of vertically spaced-apart images of the well, each image of the first plurality of spaced-apart images having a same location with respect to a horizontal plane and a different height along a Z axis, such that a first volumetric image stack is generated with respect to the well; (c) identifying, based on one or more coplanar images of the well captured at a second time substantially later than the first time, a location of a candidate colony of cells; (d) determining, based on the first volumetric image stack, a measure of likelihood (e.g., a probability and/or a distance between the cell colony and the location of one or more cells in the set of images captured at the first time) that the candidate colony is monoclonal; and (e) in response to the measure of likelihood exceeding a selected threshold (e.g., a specific probability and/or a specified distance value, such as 50 µm), picking the candidate colony using a picking head of the apparatus to isolate at least a portion of the colony.

Paragraph A0.1. The method of paragraph A0, wherein identifying the location of the candidate colony of cells is further based on criteria including a shape, a density, and/or a size of the colony.

Paragraph A0.2. The method of paragraph A0, wherein identifying the location of the candidate colony of cells is further based on a proximity of the colony to any other colonies.

Paragraph A1. The method of paragraph A0, further comprising plating the plurality of cells in the semi-solid medium, wherein the step of capturing the first plurality of images is performed less than twenty-four hours after plating.

Paragraph A2. The method of paragraph A0, further comprising: (f) capturing, prior to the second time and using the digital imaging device, a second plurality of vertically spaced-apart images of the well, such that a second volumetric image stack is generated with respect to the well; and (g) comparing the second volumetric image stack to the first volumetric image stack to determine movement (e.g., drifting) of the cells in the semi-solid medium.

Paragraph A3. The method of paragraph A0, wherein each image in the first volumetric image stack has a discrete Z-height.

Paragraph A4. The method of paragraph A3, wherein respective Z-heights of sequential images in the first volumetric image stack differ by at least approximately 20 micrometers.

Paragraph A5. The method of paragraph A4, wherein the respective Z-heights of sequential images in the first volumetric image stack differ by less than approximately 50 micrometers.

Paragraph A6. The method of paragraph A0, wherein the first volumetric image stack spans a complete depth of the semi-solid medium in the well.

Paragraph A7. The method of paragraph A0, wherein determining the measure of likelihood that the candidate colony is monoclonal comprises observing that no more than one cell was found in the first volumetric image stack within a selected radius of the candidate colony.

Paragraph A8. The method of paragraph A7, wherein determining the measure of likelihood that the candidate colony is monoclonal comprises observing how many cell location probability cones intersect a hemispherical volume defined by the selected radius of the candidate colony.

Paragraph A9. The method of paragraph A7, wherein observing that no more than one cell was found comprises observing that no fewer than one cell was found.

Paragraph A10. The method of paragraph A0, wherein identifying the candidate colony of cells comprises at least one criterion other than monoclonality.

Paragraph A11. The method of paragraph A0, wherein each image of the first plurality of spaced-apart images comprises a combined plurality of smaller images.

Paragraph A12. The method of paragraph A11, wherein the plurality of smaller images are combined by cropping and tiling based on respective known positions of the digital imaging device with respect to the horizontal plane.

Paragraph A13. The method of paragraph A0, wherein the first time and the second time differ by at least approximately ten days.

Paragraph A14. The method of paragraph A13, wherein the first time corresponds to Day Zero and the second time corresponds to day ten or later.

Paragraph A15. The method of paragraph A0, wherein the digital imaging device used to capture the first plurality of vertically spaced-apart images of the well is a first digital imaging device, and the one or more coplanar images of the well are captured at the second time using a second digital imaging device.

Paragraph A16. The method of paragraph A0, further comprising repeating the steps of capturing, identifying, determining, and picking on a second well of the sample plate.

Paragraph B0. A method for selecting one or more monoclonal cell colonies using an apparatus, the method comprising: (a) loading a sample plate onto a table of the apparatus, the sample plate including a well having a transparent base and a plurality of cells held in a semi-solid medium, wherein the well is covered by an air-permeable seal; (b) using, on Day Zero with respect to plating of the cells, a digital imaging device having an objective disposed below the table to capture a plurality of vertically spaced-apart first images of the well, each first image taken through the transparent base and having a different height along a Z axis, such that a volumetric image stack is generated with respect to the well; (c) identifying, based on one or more second images of the well captured at least five days after plating, a location of a candidate colony of cells; (d) determining, by comparing the location of the candidate colony to a corresponding location in the volumetric image stack, a measure of likelihood that the candidate colony is monoclonal; and (e) in response to the measure of likelihood exceeding a selected threshold, picking the candidate colony using a picking head of the apparatus to relocate at least a portion of the colony to a dispensing container.

Paragraph B1. The method of paragraph B0, further comprising: (f) mapping a plurality of cell locations known on Day Zero, based on the volumetric image stack; (g) identifying, from the plurality of cell locations, single cells that are spaced from all other cells by at least a selected first radius; and (h) limiting potential locations of the candidate colony of cells to locations corresponding to the identified single cells.

Paragraph B2. The method of paragraph B0, wherein comparing the location of the candidate colony to the corresponding location in the volumetric image stack comprises determining respective distances between the candidate colony and one or more individual cells locatable in the volumetric image stack.

Paragraph B3. The method of paragraph B0, wherein a magnification of the objective is between 2× and 7×.

Paragraph B4A. The method of paragraph B0, wherein a numerical aperture of the objective is between 0.1 and 0.4.

Paragraph B4B. The method of paragraph B0, wherein the objective is a dry objective.

Paragraph B5. The method of paragraph B0, wherein the one or more second images of the well are captured at least five days after plating using a second digital imaging device disposed above the table.

Paragraph B6. The method of paragraph B0, wherein the objective is positionable in three dimensions using an X-Y positioner and a Z-axis positioner, the method further comprising: (f) capturing a plurality of smaller images in an X-Y plane for each respective Z-height; and (g) combining the plurality of smaller images to produce one of the first images in the volumetric image stack.

Paragraph B7. The method of paragraph B6, wherein combining the plurality of smaller images comprises cropping and tiling the plurality of smaller images.

Paragraph B8. The method of paragraph B0, further comprising repeating the steps of using, identifying, determining, and picking on a second well of the sample plate.

Paragraph C0. A method for selecting one or more monoclonal cell colonies using an apparatus, the method comprising: (a) plating a plurality of cells in a semi-solid medium having a selected depth in a well, such that the semi-solid medium defines a volume; (b) placing the well on the apparatus and capturing, using a digital imaging device of the apparatus, a plurality of first images of the volume, each first image being parallel to and orthogonally spaced from the other first images by a discrete distance, such that the plurality of first images spans the volume; (c) incubating the well for a plurality of days following the capturing of the plurality of images; (d) following the incubation, capturing one or more second images of a single plane of the well; (e) selecting a candidate colony of cells based on the one or more second images using one or more criteria; (f) confirming monoclonality of the candidate colony of cells based on the plurality of first images; and (g) picking the candidate colony of cells using a picking head of the apparatus.

Paragraph C1A. The method of paragraph C0, wherein the plurality of first images are collected before a majority of the plurality of cells have divided.

Paragraph C1B. The method of paragraph C0, wherein the plurality of first images are collected within approximately twelve hours after the semi-solid medium has solidified.

Paragraph C1C. The method of paragraph C0, wherein a resolution of the plurality of first images allows identification of single cells.

Paragraph C1 D. The method of paragraph C0, further comprising sealing the well with an air-permeable membrane prior to incubating.

Paragraph C2. The method of paragraph C0, further comprising centrifuging the well for at least approximately five minutes at 100 times gravity prior to placing the well on the apparatus and capturing the first images.

Paragraph C3. The method of paragraph C2, further comprising adding a layer of additional semi-solid medium to the well following the step of centrifuging.

Paragraph C4. The method of paragraph C0, wherein the discrete distance between first images is less than approximately fifty micrometers.

Paragraph C5. The method of paragraph C0, wherein the first images are substantially horizontal and spaced along a vertical axis.

Paragraph C6. The method of paragraph C0, wherein confirming monoclonality of the candidate colony of cells comprises determining how many individual cells are present in the plurality of first images of the volume within a selected radius of a location of the candidate colony.

Paragraph C7. The method of paragraph C6, wherein the selected radius is constant, defining a hemispherical subvolume within the volume.

Paragraph C8. The method of paragraph C6, wherein the selected radius is variable based on height.

Paragraph C9. The method of paragraph C6, wherein confirming monoclonality further comprises determining that exactly one cell is present in the plurality of first images of the volume within the selected radius of the location of the candidate colony.

Paragraph C10. The method of paragraph C0, wherein the selected depth of the semi-solid medium is approximately one millimeter.

Paragraph C11. The method of paragraph C0, wherein the one or more criteria used to select the candidate colony comprise an intensity of fluorescence.

Paragraph D0. An apparatus for picking cell colonies comprising: (a) an apparatus bed configured to receive a sample container, wherein the sample container comprises a transparent floor supporting a volume of semi-solid medium in which a plurality of cells are present; (b) a digital camera having an objective disposed below the apparatus bed, such that digital images of the cells in the semi-solid medium are capturable through the transparent floor of the sample container; (c) a Z-axis positioner coupled to the objective and configured to position the objective at a selectable vertical height; (d) an X-Y positioner coupled to the objective and configured to position the objective at a selectable horizontal position; (e) a picking head of the apparatus to isolate at least a portion of the colony; and (f) a controller coupled to the digital camera, the Z-axis positioner, X-Y positioner, and picking head, the controller having a processor configured to execute a stored set of instructions (i) to capture a plurality of vertically spaced-apart images of the volume of semi-solid medium, each image taken through the transparent floor and having a different height along the Z axis, such that a volumetric image stack is generated, and (ii) to position the picking head to isolate at least a portion of the colony.

Paragraph D1. The apparatus of paragraph D0, wherein a magnification of the objective is between 2× and 7×.

Paragraph D2. The apparatus of paragraph D0, wherein a numerical aperture of the objective is between 0.1 and 0.4.

Paragraph D3. The apparatus of paragraph D0, wherein the objective is a dry objective.

Paragraph D4. The apparatus of paragraph D0, wherein successive heights of the vertically spaced-apart images differ by no more than approximately 50 micrometers.

Paragraph D5. The apparatus of paragraph D0, the sample container comprising a well of a multiwell plate, wherein the processor is further configured to execute the stored set of instructions on another well of the multiwell plate.

Paragraph D6. The apparatus of paragraph D0, wherein the image of a single cell occupies at least about four pixels of the digital camera.

Example 7. Selected Embodiments 2

This example describes yet further aspects and features of cell colony selection, analysis, and picking methods, presented without limitation as a series of indexed paragraphs.

Paragraph E0. A method for selecting one or more monoclonal cell colonies using an apparatus having a digital imaging device, the method comprising: (a) loading a sample plate onto the apparatus, the sample plate including a well having a plurality of cells held in a semi-solid medium; (b) capturing, at a first time and using the digital imaging device, a first plurality of vertically spaced-apart images of the well, each image having a different height along a Z axis, such that a volumetric image stack (or Z stack) is generated with respect to the well; (c) identifying, based on one or more images of the well captured at a second time substantially later than the first time, a location of a candidate colony of cells; (d) determining, based on the volumetric image stack, a measure of likelihood that the candidate colony is monoclonal; and (e) in response to the determined measure of likelihood, picking the candidate colony using a picking head of the apparatus to isolate at least a portion of the colony.

Paragraph E1. The method of paragraph E0, further comprising a step of plating the plurality of cells in the semi-solid medium, wherein the step of capturing a first plurality of images is performed less than twenty-four hours after plating.

Paragraph E2. The method of paragraph E1, wherein the step of capturing a first plurality of images is performed less than six hours after plating.

Paragraph E3. The method of paragraph E1 or E2, further comprising centrifuging the well containing the plated cells between the step of plating the plurality of cells and the step of loading a sample plate onto the apparatus.

Paragraph E4. The method of paragraph E3, wherein the step of centrifuging the well is performed for at least three minutes and with a centrifugal force of at least 50 times the force of gravity.

Paragraph E5. The method of paragraph E4, wherein the step of centrifuging the well is performed for about five minutes with a centrifugal force of about 100 times the force of gravity.

Paragraph E6. The method of any of paragraphs E3-E5, further comprising a step of adding additional semi-solid medium to the well after the step of centrifuging.

Paragraph E7. The method of any preceding paragraph, further comprising a step of covering the well with an air-permeable seal before the step of loading the plate.

Paragraph E8. The method of any preceding paragraph, wherein a depth of the semi-solid medium in the well is no more than approximately one millimeter.

Paragraph E9. The method of any preceding paragraph, wherein respective Z-coordinates of sequential images in the volumetric image stack differ by at least approximately 20 micrometers.

Paragraph E10. The method of paragraph E9, wherein the respective Z-coordinates of sequential images in the volumetric image stack differ by less than approximately 50 micrometers.

Paragraph E11. The method of paragraph E10, wherein the respective Z-coordinates of sequential images in the volumetric image stack differ by between 25 micrometers and 45 micrometers.

Paragraph E12. The method of any preceding paragraph, wherein the volumetric image stack spans an entire depth of the semi-solid medium in the well. Collecting images over the entire depth of medium may be desirable, even though the method of paragraph E0 covers scanning just a portion of the depth, because scanning the entire depth provides information on the locations of as many cells as possible, potentially increasing the reliability of the method.

Paragraph E13. The method of any preceding paragraph, wherein the first plurality of images are collected before a majority of the plurality of cells have divided.

Paragraph E14. The method of any preceding paragraph, wherein the first plurality of images are collected within approximately six hours after the semi-solid medium has gelled.

Paragraph E15. The method of any preceding paragraph, wherein a resolution of the first plurality of images allows identification of single cells.

Paragraph E16. The apparatus of paragraph E15, wherein an image of a single cell occupies at least about four pixels of the digital imaging device.

Paragraph E17. The method of any preceding paragraph, wherein the well has a transparent base, and wherein the digital imaging device has an objective disposed below the base.

Paragraph E18. The method of paragraph E17, wherein a magnification of the objective is between 2× and 7×.

Paragraph E19. The method of paragraph E17 or E18, wherein a numerical aperture of the objective is between 0.1 and 0.4.

Paragraph E20. The method of any of paragraphs E17-E19, wherein the objective is a dry objective.

Paragraph E21. The method of any preceding paragraph, wherein each image of the first plurality of images comprises a combined plurality of smaller images all captured at the same Z-height.

Paragraph E22. The method of paragraph E21, wherein the plurality of smaller images are combined based on respective known positions of the digital imaging device with respect to a horizontal plane.

Paragraph E23. The method of any preceding paragraph, further comprising: (f) mapping a plurality of cell locations based on the volumetric image stack; (g) identifying, from the plurality of cell locations, single cells that are spaced from all other cells by at least a selected first distance (e.g., 50 μm); and (h) limiting potential locations of the candidate colony of cells to locations corresponding to the identified single cells (i.e., excluding potential locations that otherwise would be acceptable if the locations are not spaced by at least the selected first distance from all other cells).

Paragraph E24. The method of any preceding paragraph, the volumetric image stack being a first volumetric stack, further comprising: (f) capturing, before the second time and using the digital imaging device, a second plurality of vertically spaced-apart images of the well, such that a second volumetric image stack is generated with respect to the well; and (g) comparing the second volumetric image stack to the first volumetric image stack to determine movement of the cells in the semi-solid medium.

Paragraph E25. The method of any preceding paragraph, wherein the digital imaging device used to capture the first plurality of vertically spaced-apart images of the well is a first digital imaging device, and the one or more images of the well are captured at the second time using a second digital imaging device.

Paragraph E26. The method of paragraph E25, wherein the second digital imaging device is disposed above the well.

Paragraph E27. The method of any preceding paragraph, wherein the first time and the second time differ by at least ten days.

Paragraph E28. The method of any preceding paragraph, wherein the step of identifying a location of a candidate colony of cells further comprises at least one criterion other than monoclonality.

Paragraph E29. The method of paragraph E28, wherein the at least one criterion is selected from the group consisting of a shape, a density, and a size of the colony.

Paragraph E30. The method of paragraph E28 or E29, wherein the at least one criterion is based at least in part on a proximity of the candidate colony to any other colonies of cells.

Paragraph E31. The method of paragraph E28, wherein the at least one criterion includes an intensity of fluorescence from the candidate colony.

Paragraph E32. The method of any preceding paragraph, wherein the step of determining a measure of likelihood that the candidate colony is monoclonal comprises a step of observing that no more than one cell was found in the volumetric image stack within a selected distance of the location of the candidate colony.

Paragraph E33. The method of paragraph E32, wherein the distance is no more than about 50 μm.

Paragraph E34. The method of paragraph E0, wherein the step of determining a measure of likelihood that the candidate colony is monoclonal comprises observing how many cell location probability cones intersect a hemispherical volume defined by the selected distance of the candidate colony.

Paragraph E35. The method of any preceding paragraph, wherein the step of determining a measuring of likelihood that the candidate colony is monoclonal comprises a step of comparing the location of the candidate colony to a corresponding location in the volumetric image stack.

Paragraph E36. The method of paragraph E35, wherein the step of comparing the location of the candidate colony to a corresponding location in the volumetric image stack comprises a step of evaluating respective distances between the candidate colony and one or more individual cells locatable in the volumetric image stack.

Paragraph E37. The method of any preceding paragraph, further comprising a step of relocating at least a portion of a colony to a dispensing container, after the step of picking.

Paragraph E38. The method of any preceding paragraph, further comprising repeating the steps of capturing, identifying, determining, and picking on a second well of the sample plate.

F0. An apparatus for picking cell colonies, comprising: (a) an apparatus bed configured to receive a sample container, wherein the sample container comprises a transparent base supporting a volume of semi-solid medium in which a plurality of cells are present; (b) a digital camera having an objective disposed below the apparatus bed, such that digital images of the cells in the semi-solid medium are capturable through the transparent base of the sample container; (c) a Z-axis positioner coupled to the objective and configured to position the objective at a selectable vertical height; (d) a picking head of the apparatus to isolate at least a portion of the colony; and (e) a controller coupled to the digital camera, the Z-axis positioner, and picking head, the controller having a processor configured to execute a stored set of instructions (i) to capture a plurality of vertically spaced-apart images of the volume of semi-solid medium, each image taken through the transparent base and having a different height along the Z axis, such that a volumetric image stack is generated, and (ii) to position the picking head to isolate at least a portion of the colony.

Paragraph F1. The apparatus of paragraph F0, further comprising an X-Y positioner coupled to the objective and the controller and configured to position the objective at a selectable horizontal position.

Paragraph F2. The apparatus of paragraph F0 or F1, wherein the plurality of vertically spaced-apart images are captured at a first time, and wherein the processor is further configured to execute a stored set of instructions to capture one or more images of the volume of semi-solid medium at a second time substantially later than the first time.

Paragraph F3. The apparatus of any of paragraphs F0 to F2, wherein the image of a single cell occupies at least about four pixels of the digital camera.

CONCLUSION

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method for selecting one or more monoclonal cell colonies using an apparatus having a digital imaging device, the method comprising:
    loading a sample plate onto the apparatus, the sample plate including a well having a plurality of originator cells plated in a semi-solid medium;
    capturing, at a first time on day zero and using the digital imaging device, a first plurality of vertically spaced-apart images of the well, each image having a different height along a Z axis, such that a first volumetric image stack is generated with respect to the well;
    capturing, at a second time between day zero and pick day and using the digital imaging device, a second plurality of vertically spaced-apart images of the well, such that a second volumetric image stack is generated with respect to the well; and
    comparing the second volumetric image stack to the first volumetric image stack to determine movement of the cells in the semi-solid medium;
    identifying, based on one or more images of the well captured at the second time later than the first time, a location of a candidate colony of cells;
    determining, based on the first volumetric image stack, a measure of likelihood that the candidate colony is monoclonal based on a monoclonal selection criterion comprising
        mapping a plurality of originator cell locations based on the first volumetric image stack;
        identifying, from the plurality of originator cell locations, single originator cells that are spaced from all other cells by at least a selected first distance; and
        limiting potential locations of the candidate colony of cells to locations corresponding to the identified single originator cells; and
    in response to the determined measure of likelihood, compiling a pick list of colony coordinates based on locations of colonies satisfying the monoclonal selection criterion, and picking the candidate colony using a picking head of the apparatus to isolate at least a portion of the colony.

2. The method of claim 1, further comprising a step of plating the plurality of originator cells in the semi-solid medium, wherein the step of capturing a first plurality of images is performed less than twenty-four hours after plating.

3. The method of claim 2, wherein the step of capturing a first plurality of images is performed less than six hours after plating.

4. The method of claim 2, further comprising centrifuging the well containing the plated originator cells between the step of plating the plurality of cells and the step of loading a sample plate onto the apparatus.

5. The method of claim 4, wherein the step of centrifuging the well is performed for at least three minutes and with a centrifugal force of at least 50 times the force of gravity.

6. The method of claim 5, wherein the step of centrifuging the well is performed for about five minute s with a centrifugal tome of about 100 times the force of gravity.

7. The method of claim 4, further comprising a step of adding additional semi-solid medium to the well after the step of centrifuging.

8. The method of claim 1, further comprising a step of covering the well with an air-permeable seal before the step of loading the plate.

9. The method of claim 1, wherein a depth of the semi-solid medium in the well is no more than approximately one millimeter.

10. The method of claim 1 wherein respective Z-coordinates of sequential images in the volumetric image stack differ by at least approximately 20 micrometers.

11. The method of claim 10, wherein the respective Z-coordinates sequential images in the volumetric image stack differ by less than approximately 50 micrometers.

12. The method of claim 11, wherein the respective Z-coordinates of sequential images in the volumetric image stack differ by between 25 micrometers and 45 micrometers.

13. The method of claim 1, wherein the volumetric image stack spans an entire depth of the semi-solid medium in the well.

14. The method of claim 1, wherein the first plurality of images are collected before a majority of the plurality of originator cells have divided.

15. The method claim 1, wherein the first plurality of images are collected within approximately six hours slier the semi-solid medium has gelled.

16. The method of claim 1, wherein the capturing at the first nine comprises resolving the first plurality of images to identify single originator cells.

17. The method of claim 16, wherein the resolved images of the single originator cells each occupy at least about four pixels of the digital imaging device.

18. Method of claim 1, wherein the well has a transparent base, and wherein the digital imaging device has an objective disposed below the base.

19. The method of claim 18, wherein a magnification of the objective is between 2× and 7×.

20. The method of claim 18, wherein a numerical aperture of the objective is between 0.1 and 0.4.

21. The method of claim 18, wherein the objective is a dry objective.

22. The method of claim 1, wherein each image of the first plurality of images comprises a combined plurality of smaller images all captured at the same height along the Z-axis.

23. The method of claim 22, wherein the plurality of smaller images are combined based on respective known positions of the digital imaging device with respect to a horizontal plane.

24. The method of claim 1, wherein the selected first distance is 50 µm.

25. The method of claim 1, wherein the digital imaging device used to capture the first plurality of vertically spaced-apart images of the well is a first digital imaging device, and the one or more images of the well are captured at the second time using a second digital imaging device.

26. The method of claim 25, wherein the second digital imaging device is disposed above the well.

27. The method of claim 1, wherein the first time and the second time differ by at least ten days.

28. The method of claim 1, wherein the step of identifying a location of a candidate colony of cells further comprises at least one criterion other than monoclonality.

29. The method of claim 28, wherein the at least one criterion is selected from the group consisting of a shape, a density, and a size of the colony.

30. The method of claim 28, wherein the at least one criterion is based at least in part on a proximity of the candidate colony to any other colonies of cells.

31. The method of claim 28, wherein the at least one criterion includes an intensity of fluorescence from the candidate colony.

32. The method of claim 1, wherein the step of determining a measure of likelihood that the candidate colony is monoclonal comprises a step of observing that no more than one originator cell was found in the volumetric image stack within a selected distance of the location of the candidate colony.

33. The method of claim 32, wherein the distance is no more than about 50 µm.

34. The method of claim 1, wherein the step of determining a measure of likelihood that the candidate colony is monoclonal comprises
correlating the position of the candidate colony in a pick day image with the position of each of the plurality of single originator cells in a day zero volumetric image stack and cell movement downward drift over time comprising
determining a cell location probability cone for each of the single originator cells in the day zero volumetric image stack, wherein each cell location probability cone comprises an inverted cone with its apex at a starting position of one of the single originator cells;
determining a hemisphere defined by a selected radius centered on the candidate colony; and
observing how many cell location probability cones intersect the hemispherical volume defined by the selected radius centered on the candidate colony,
wherein the determining the measure of likelihood that the candidate colony is monoclonal comprises observing that no more than one originator cell was found in the first volumetric stack within the selected radius centered on the candidate colony.

35. The method of claim 1, wherein the step of determining a measuring of likelihood that the candidate colony is monoclonal comprises a step of comparing the location of the candidate colony to a corresponding location in the volumetric image stack.

36. The method of claim 35, wherein the step of comparing the location of the candidate colony to a corresponding location in the volumetric image stack comprises a step of evaluating respective distances between the candidate colony and one or more individual cells locatable in the volumetric image stack.

37. The method of claim 1, further comprising a step of relocating at least a portion of a colony to a dispensing container, after the step of picking.

38. The method of claim 1, further comprising repeating the steps of capturing, identifying, determining, and picking on a second well of the sample plate.

39. The method of claim 34, further comprising
imaging the well from day 1 to pick day minus 1; and
confirming the cell movement downward drift over time by comparing images taken from day 1 to pick day minus 1.

40. The method of claim 34, wherein the pick day is 10-14 days after day zero.

41. The method of claim 1, wherein the second time is from day 1 to pick day minus 1.

* * * * *